(12) United States Patent
Bentz et al.

(10) Patent No.: US 6,338,235 B1
(45) Date of Patent: Jan. 15, 2002

(54) METHOD OF PRODUCING PACKAGING CONTAINERS WITH LOW BACTERIA CONTAMINATION

(75) Inventors: Christer Bentz, Hjärup; Mats Andersson, Ängelholm, both of (SE)

(73) Assignee: Tetra Laval Holdings & Finance S.A., Pully (CH)

( * ) Notice: Subject to any disclaimer, the term of this patent is extended or adjusted under 35 U.S.C. 154(b) by 0 days.

(21) Appl. No.: 09/531,889

(22) Filed: Mar. 21, 2000

(30) Foreign Application Priority Data

Apr. 21, 1999 (SE) ................................................ 9901421

(51) Int. Cl.⁷ ............................................. B65B 55/04
(52) U.S. Cl. ........................................... 53/426; 53/140
(58) Field of Search ..................... 53/140, 243, 452, 53/459, 478, 426

(56) References Cited

U.S. PATENT DOCUMENTS

| | | | | |
|---|---|---|---|---|
| 4,129,467 A | * | 12/1978 | Knutsson | 156/84 |
| 4,495,209 A | * | 1/1985 | Whitside | 426/392 |
| 4,564,139 A | * | 1/1986 | Reil | 229/5.5 |
| 4,584,823 A | * | 4/1986 | Nagel | 53/453 |
| 4,659,415 A | * | 4/1987 | Shi mokawa et al. | 156/379.7 |
| 4,742,667 A | * | 5/1988 | Muller et al. | 53/167 |
| 5,074,099 A | * | 12/1991 | Andersson et al. | 53/410 |
| 5,350,568 A | * | 9/1994 | Tuckner et al. | 422/300 |
| 5,885,515 A | * | 3/1999 | Hudkins | 264/516 |

FOREIGN PATENT DOCUMENTS

| | | |
|---|---|---|
| EP | 0 093 849 | 6/1988 |
| EP | 0 217 282 | 12/1990 |
| EP | 0 492 140 | 7/1992 |
| NO | 125804 | 11/1972 |
| SE | 340 591 | 11/1971 |
| WO | 96/18541 | 6/1996 |

* cited by examiner

*Primary Examiner*—Scott A. Smith
*Assistant Examiner*—Chukwurah Nathaniel
(74) *Attorney, Agent, or Firm*—Burns, Doane, Swecker & Mathis, L.L.P.

(57) ABSTRACT

The disclosure relates to a method of producing, from laminated paper/plastic material, a packaging container with low bacteria contamination which is reformed into a tubular container blank and is provided with an end wall by injection moulding of thermoplastic material at a temperature of at least 200° C., whereafter the interior of the container is subjected to a bacteria-reducing treatment based on a chemical reaction and/or bactericidal irradiation and is filled with the desired contents, and also sealed.

7 Claims, 1 Drawing Sheet

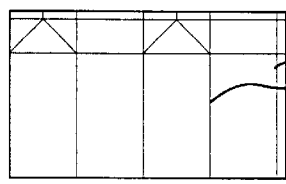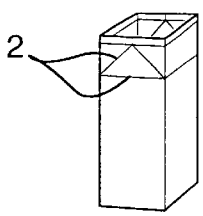
Fig 1A    Fig 1B
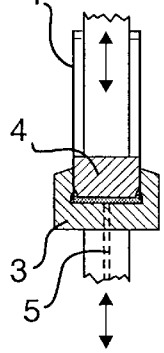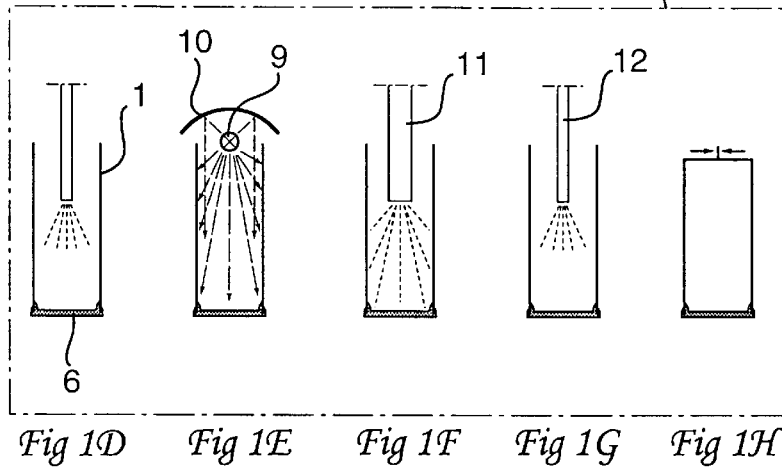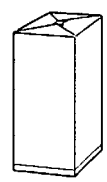
Fig 1C    Fig 1D    Fig 1E    Fig 1F    Fig 1G    Fig 1H    Fig 1I
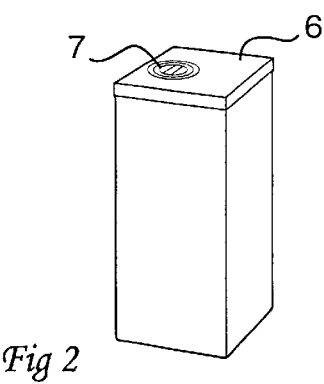
Fig 2

METHOD OF PRODUCING PACKAGING CONTAINERS WITH LOW BACTERIA CONTAMINATION

TECHNICAL FIELD

The present invention relates to a method of producing a packaging container with low bacteria contamination.

BACKGROUND ART

Packaging containers of single-use disposable type are employed for packing different types of consumer products, e.g. foods such as milk or juice. In such instance, use is normally made of packaging containers which have been manufactured from a laminated material comprising layers of paper and thermoplastic, and possibly additional layers of metal foil or some other barrier material, e.g. barrier plastic. The packaging containers are manufactured in that the packaging laminate, in web or sheet form, is reformed into hose or tube form, provided with a first end closure seal and filled with the desired contents, being finally sealed at the other end.

Packaging containers of the above-mentioned or similar type are used, for example, for packing pasteurised milk. The filled and sealed package must, in this instance, be stored in cold storage, for example at a maximum temperature of +8° C. and will then have a shelf life of 6 to 8 days. This shelf life is generally sufficient in the packing of perishable goods and in handling in an existing, unbroken refrigeration chain, i.e. immediate cooling after filling and sealing, transport in refrigerated vehicles and exposure for sale in refrigerated display counters.

When the intention is to pack milk or other food products so that they obtain a longer shelf life and/or can be handled and transported without the requirement of refrigeration, use is made of so-called aseptic packaging containers which, prior to filling with the desired contents, are subjected to a bactericidal treatment. In this instance, for example a chemical sterilisation agent may be used, such as hydrogen peroxide ($H_2O_2$) or the packaging container may also be subjected to some form of irradiation sterilisation, for example in that its interior is illuminated with UV light of suitable, bactericidal wavelength (combinations of other methods may possibly also be employed). When a thus treated packaging container is ready for filling with its contents, the bacterial contamination level has been reduced to such an extent that no growth of bacteria can thereafter take place, naturally on condition that the contents have also been sterilised beforehand, for example by heat treatment to such a temperature that the contents are in practice bacteria-free. When the thus treated packaging container, under sterile conditions, has been filled with the sterile contents and sealed, the package will have a shelf life of several months; in certain cases, for example in the packing of less sensitive products such as, for instance, orange juice, a shelf life of up to a year. Moreover, this shelf life will be obtained without any demands needing to be placed on cold storage or handling of the package under special conditions.

In recent years, aseptic packages produced in the above-outlined manner for, for instance, dairy produce have enjoyed increasing expansion in use, in particular in countries where—because of the climate and level of development—it is not possible to ensure that the packages can be handled and stored under refrigerated conditions. However, the sterilising treatment of both the packaging containers and their contents renders production more complicated and more expensive, and since it has proved in practice that, in many countries, only a fraction of the maximum shelf life is used, there has arisen a need for a package which, from the point of view of shelf life, is an intermediate stage between the original, unsterile packaging container type for pasteurised contents and the aseptic package displaying extremely long shelf life. This compromise, which makes for a slightly longer shelf life than non-aseptic packages but, at the same time, may be produced employing considerably less of a technical input and at a considerably lower cost, is normally entitled "extended shelf life" (ESL). Such a package is subjected to a limited, bacteria-reducing treatment and is filled with contents which are not sterile, but handled under such safety regulations that the bacteria contamination is extremely low. In such instance, it is possible to achieve a shelf life of 4 to 6 weeks (depending on the product), on condition that the packaging container is handled in the refrigerated state.

In the prior art production of packaging containers of this ESL type, a bacteria-reducing treatment of the packaging container takes place without achieving the level of sterility which is the case in so-called aseptic packaging containers. In the treatment of, for example, a packaging material web, it will here be possible, on the one hand, to carry out more rapid treatment, and on the other hand to reduce the input as regards, for example, the concentration of the sterilisation agent employed (hydrogen peroxide) or the time for the irradiation treatment in irradiation sterilisation as compared with that which is required for producing an aseptic package of the above-mentioned type. In the bacteria-reducing treatment of already partly finished packaging containers, for example the type of packaging container which is described in European Patent Specification 217.282, it has, however, in practice proved to require a relatively long time, or alternatively sterilisation agent at a high concentration in order to ensure a satisfactory level of bacteria destruction. The design of, for example, the bottom of the packaging container with a plurality of partly overlapping, folded wall sections gives uneven, complicated forms and pockets adjacent the folding and sealing regions which are difficult to sterilise with the desired outcome. However, it has here proved that the gain which could theoretically be attained by reducing the requirements from the level stipulated for the production of aseptic packaging containers to the level which is necessary for the production of "extended shelf life" packaging containers cannot be achieved in practice. As a result, the advantages in prospect will not materialise, since, for example, a more highly concentrated chemical sterilisation agent will also be more difficult to remove and thereby requires higher temperatures and/or longer times to ensure low residual quantities, which is a manifest disadvantage also from the point of view of energy and economics. Since all of these drawbacks are related to the presence of pockets and mutually overlapping material areas, in particular at the bottom region of the packaging container, it would appear that the sought-for advantages could be attained if only the packaging design and construction is such that the bottom of the packaging container becomes more planar and free from concealed areas, and is preferably also produced in such a manner that the bacteria contamination or loading will be relatively slight already from the outset.

OBJECTS OF THE INVENTION

One object of the present invention is to realise a method of producing a packaging container with low bacteria contamination, the method making it possible to simplify and speed up the bacteria-reducing treatment of the packaging container.

A further object of the present invention is to realise a method of producing a packaging container with low bacteria contamination, the method realising a packaging container of such construction and configuration that the bacteria-reducing treatment may be made both simpler and quicker than has hitherto been the case.

Yet a further object of the present invention is to realise a method of producing a packaging container, the method of production having been adapted and optimised in order to simplify the subsequent, bacteria-reducing treatment of the interior of the packaging container.

Still a further object of the present invention is, finally, to realise a method of producing a packaging container with low bacteria contamination, the method both simplifying and economising the production of the finished packaging container and obviating the drawbacks inherent in prior art methods.

BRIEF DESCRIPTION OF THE ACCOMPANYING DRAWING

One preferred embodiment of the method according to the present invention will now be described in greater detail hereinbelow, with particular reference to the accompanying, schematic Drawing which shows only those parts and details indispensable to an understanding of the present invention. In the accompanying Drawing:

FIGS. 1A–I show in steps the production of a packaging container with low bacteria contamination following the method according to the present invention; and FIG. 2 is a perspective view of a packaging container produced following the method according to the present invention.

DESCRIPTION OF PREFERRED EMBODIMENT

FIG. 1 shows how a packaging container blank 1 is displaced stepwise between different processing stations and is progressively reformed into a packaging container filled with its contents and sealed, the packaging container having extended shelf life. The packaging container blank 1 is of the type which is, for example, employed for the production of packaging containers which are marketed under the trademark Tetra Top®. Such a packaging container, as well as the method for its production and a machine for carrying the method into effect, are disclosed in European Patent Specification EP 93849, to which reference is now made. This type of packaging container is, like many other packaging containers for, for instance milk or juice, produced from a laminated packaging material which includes a central carrier or core layer of, for example, fibrous material such as paper or the like, as well as layers applied on either side thereof, consisting of thin, liquid-tight plastic material, for example a thermoplastic such as polyethylene. The packaging material may also include additional layers, e.g. layers of gas-tight material such as aluminium foil (Alifoil) or some type of barrier plastic. The packaging container blank 1 illustrated in FIG. 1 is manufactured from this type or a similar type of material which, from an earlier (not shown) web-shape, has been cut into suitable dimensions. The blank includes a pattern of crease lines 2, which facilitate folding of the blank 1 into the form of a tube of rectangular or square cross section (FIG. 2B). In such instance, the blank is sealed to itself by thermosealing, which is possible thanks to the outer layer of thermoplastic of the material. In at least one of the end regions of the tubular packaging container blank 1 (the upper end, FIG. 1B), the blank displays additional crease lines 2 extending obliquely over the blank and being utilised for defining a number of end flaps which, after filling of the packaging container, are utilised, by folding and thermosealing, to form a tight end wall which thus forms the bottom of the finished packaging container.

According to the present invention, the packaging container blank 1 is provided with a top by injection moulding of a thermoplastic material, which takes place with the aid of outer and inner mould halves 3 and 4 (FIG. 1C). More precisely, the tubular blank is placed on the inner mould half 4 which is in the form of a mandrel whose end is profiled in a suitable manner to form a part of an injection mould. The blank placed on the inner mould half 4 or the mandrel is thereafter moved with its one end (subsequently the upper end) into the outer mould half 3 (which may be of duplex design if required) until such time as its upper edge sealingly abuts against the outside of the blank. The mould half 3 has a profiled bottom surface which forms the other half of the mould. The two mould halves 3 and 4 thus sealingly surround the top end of the tubular packaging container blank 1 and, via a channel 5 in the one mould half 3, thermoplastic material is thereafter injected at a temperature of approx. 220° C. in the thus formed mould. The material fills out the mould cavity between the two mould halves and also penetrates out to and surrounds the top edges of the tubular packaging container blank 1 so that a liquid-tight and permanent seal is formed between the end wall 6 formed by the injection moulding and the packaging container blank. The profile of the mould halves 3 and 4 may here be such that there is created, in the end wall 6 (FIG. 2), a suitable opening arrangement 7 which, for instance, may be formed by constrictions in the mould halves 3, 4 which together form a weakened, annular tearing region. The end wall may also include parts of the laminated material of the tubular blank, e.g. inwardly folded edge portions which surround an openable, injection moulded part. The opening arrangement 7 may possibly also be provided with some form of outer handle or projecting gripping member. However, it is essential according to the present invention that the inner surface of the end wall 6, i.e. the surface which will subsequently come into contact with the contents of the packaging container, is relatively planar and free of depressions or irregularities which may impede subsequent, bacteria-reducing treatment.

When the tubular packaging container blank 1 has been provided with the end wall 6 by injection moulding, it is moved from the injection moulding station illustrated in FIG. 1C into a closed space or chamber 8 which surrounds a number of processing stations for the blank located sequentially after one another, after the injection moulding station. The chamber 8 may, in a per se known manner, be entirely enclosed or be a chamber provided with controlled outlet which is continuously supplied with sterile air under excess pressure (possibly heated) for ensuring that the bacteria concentration in the chamber is low. As is apparent from FIG. 1, the chamber 8 comprises, in the preferred embodiment of the method according to the present invention as shown in the Figures, five processing stations. The first of these is a station in which the packaging container blank 1 is subjected to a bacteria-reducing treatment in that a sterilising chemical agent in gas or vapour form is fed to the interior of the packaging container blank. Preferably, use is here made of hydrogen peroxide at a concentration of 0.5–1 percent which, after heating to a temperature of approx. 200° C., is fed to the packaging container blank whose interior will here be heated to a temperature of approx. 110° C. The inside of the packaging container blank 1 will here be coated with a thin layer of sterilisation agent.

The packaging container blank is thereafter moved to a subsequent station (FIG. 1E) in which the interior of the blank is subjected to an irradiation sterilisation which preferably takes place with the aid of UV light from a lamp 9 for UV light extending wholly or partly down into the packaging container blank 1. The lamp may possibly be placed above the packaging container blank and there utilise a reflector 10 for ensuring that the light beams reach all interior parts of the packaging container blank 1. Since the bacteria-reducing treatment in stations D and E takes place immediately after the injection moulding of the end wall 6 of the packaging container blank 1 (within the space of only a few seconds), the end wall 6 will, when it leaves the station E for irradiation sterilisation, still be at a plastic temperature of between 80 and 100° C. The absence of pockets and folds at the inside of the end wall 6 further ensures that both the chemical sterilisation agent and the irradiation reach and are permitted to act on all parts of the inside of the packaging container blank 1. Possibly, exclusively chemical or exclusively irradiation sterilisation may be employed, which, however, is probably likely to require a certain modification of concentrations, temperatures or sterilisation times.

Once the actual bacteria-reducing treatment has been completed, the packaging container blank is moved to a subsequent station (FIG. 1F) in which sterile (filtered) hot air at a temperature of approx. 60° C. is aspirated via an air pipe 11 down into the package for flushing it clean of residues of sterilisation agent. After a suitable treatment time, the packaging container blank 1 is moved to a subsequent station (FIG. 1G) in which a filler pipe 12 supplies the desired contents, e.g. milk, to the package. As soon as the desired volume of contents has been filled into the package, this is displaced another step (FIG. 1H) in which station the container package is sealed in liquid-tight fashion at its upwardly facing bottom end in that the bottom fold panels defined by means of the crease lines 2 are mechanically folded together and thermosealed to one another. Both the bottom fin formed in this instance and the flat-laid corner flaps which occur for reasons of geometry are folded down to the end wall of the package so that the packaging container obtains a substantially planar bottom surface. The package is thereafter discharged out of the chamber 8 and righted so that the end wall 6 formed by injection moulding is turned upwards and forms the top surface of the packaging container.

The method according to the present invention has, as described above, in practice proved to make it possible to produce packaging containers with extended shelf life with the aid of a minimum input of bacteria-reducing type. The employment of injection moulding to form the end wall (or alternatively a part of an end wall, e.g. an opening arrangement) in the packaging container makes it possible, in one single phase (i.e. without the separate handling such as folding, forming and sealing which have an unfavourable effect on the bacteria concentration) to form the end wall with a relatively smooth inner surface which is free of folds and sealings which have a dirt-attraction effect and which impede sterilisation, regardless of whether this takes place with the aid of chemical sterilisation agent or by irradiation (or alternatively combinations thereof). The fact that subsequent, bacteria-reducing treatment takes place immediately after injection moulding of the end wall 6 also entails that the end wall—which after all is injection moulded at a plastic temperature of approx. 220° C. and thereby may in practice be considered as sterile—maintains a considerably elevated temperature during the first part of its passage through the chamber 8. The probability that surviving bacteria exist in the package is thus slight, and after the supplementary, bacteria-reducing treatment with both chemical sterilisation agent and irradiation, the bacteria concentration of the interior of the package as a whole has been reduced to such a level that the requirements for a packaging container with extended shelf life have been more than satisfied. At the same time, this can be achieved with a relatively rapid handling and, moreover, low concentration of chemical sterilisation agent (0.5–1 percent $H_2O_2$), which may be compared with a concentration of approx. 3 percent which is employed in the production of packaging containers with extended shelf life of the so-called gable top type, i.e. of the type which is provided with an end wall by folding and sealing of the packaging laminate. This is a major advantage which not only reduces costs and the treatment time but also facilitates the removal of sterilisation agent from the interior of the packaging container so that the risk of residual quantities of sterilisation agent in the packaging container is reduced to a minimum.

What is claimed is:

1. A method of producing a packaging container with low bacteria contamination, comprising the steps of:

reforming a sheet of laminated paper/plastic material into a tubular container blank;

providing the reformed tubular container blank with an end wall by injection molding of thermoplastic material;

subjecting the interior of the container to a bacteria-reducing treatment by way of a hydrogen peroxide with the aid of UV irradiation;

filling the container with contents; and sealing the container.

2. The method as claimed in claim 1, wherein the step of injection molding the end wall is performed by introducing a thermoplastic material at a temperature of at least 200° C. between mold halves which also surround a part of the container.

3. The method as claimed in claim 1, wherein the packaging container is, in connection with the injection molding, provided with an opening arrangement which is integrated in and comprises a part of or the whole of the end wall.

4. The method as claimed in claim 1, wherein a side of the end wall facing towards the interior of the packaging container is formed to be substantially planar.

5. The method as claimed in claim 1, wherein the bacteria-reducing treatment takes place in sequence immediately after the injection molding while the injection molded part is at a temperature exceeding 100° C.

6. The method as claimed in claim 1, wherein the bacteria-reducing treatment, as well as subsequent filling and sealing steps, take place in a protective atmosphere.

7. The method as claimed in claim 1, wherein the bacteria-reducing treatment, as well as subsequent filling and sealing operations, take place in an enclosed space.

* * * * *